United States Patent
Wang et al.

(10) Patent No.: US 9,151,718 B2
(45) Date of Patent: Oct. 6, 2015

(54) ILLUMINATION SYSTEM WITH TIME MULTIPLEXED SOURCES FOR RETICLE INSPECTION

(71) Applicant: KLA-Tencor Corporation, Milpitas, CA (US)

(72) Inventors: Daimian Wang, Fremont, CA (US); Tao-Yi Fu, Fremont, CA (US); Damon F. Kvamme, Los Gatos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 41 days.

(21) Appl. No.: 13/782,785

(22) Filed: Mar. 1, 2013

(65) Prior Publication Data
US 2013/0242295 A1    Sep. 19, 2013

Related U.S. Application Data (60) Provisional application No. 61/612,640, filed on Mar. 19, 2012, provisional application No. 61/622,281, filed on Apr. 10, 2012, provisional application No. 61/652,710, filed on May 29, 2012, provisional application No. 61/652,722, filed on May 29, 2012.

(51) Int. Cl.
*G01N 21/00* (2006.01)
*G01N 21/88* (2006.01)
*G01N 21/956* (2006.01)

(52) U.S. Cl.
CPC .......... *G01N 21/8806* (2013.01); *G01N 21/956* (2013.01); *G01N 2021/95676* (2013.01)

(58) Field of Classification Search
CPC ............... G01B 11/27; G01B 2290/70; G01B 9/02044; G01B 9/02091; G02B 6/29311; G02B 6/29362; G02B 6/29365; G02B 6/2938; G02B 6/4215; G02B 6/4227; G02B 27/0994; G02B 19/0028; G02B 19/0057; G02B 21/003
See application file for complete search history.

(56) References Cited

U.S. PATENT DOCUMENTS 4,097,115 A    6/1978  Garwin et al.
6,195,201 B1   2/2001  Koch et al.
(Continued)

FOREIGN PATENT DOCUMENTS

JP    200570090 A  *  3/2005
WO   2011080019 A1    7/2011

OTHER PUBLICATIONS

Katsuhiko Murakami et al., Development of optics for EUV lithography tools, Emerging Lithographic Technologies XI, edited by Micheal J. Lercel, Proc. of SPIE, vol. 6517, 65170J, (2007) doi: 10.1117/12.711738, 8 pages.

*Primary Examiner* — Michael P Stafira
(74) *Attorney, Agent, or Firm* — Suiter Swantz pc llo (57) ABSTRACT

The disclosure is directed to a system and method of providing illumination for reticle inspection. According to various embodiments of the disclosure, a multiplexing mirror system receives pulses of illumination from a plurality of illumination sources and directs the pulses of illumination along an illumination path to a plurality of field mirror facets. The field mirror facets receive at least a portion of illumination from the illumination path and direct at least a portion of the illumination to a plurality of pupil mirror facets. The pupil mirror facets receive at least a portion of illumination reflected from the field mirror facets and direct the portion of illumination along a delivery path to a reticle for imaging and/or defect inspection.

32 Claims, 12 Drawing Sheets

(56) References Cited

U.S. PATENT DOCUMENTS

| | | |
|---|---|---|
| 6,396,068 B1 | 5/2002 | Sweatt et al. |
| 6,861,656 B2 | 3/2005 | Murakami |
| 7,183,565 B2 | 2/2007 | Goldstein et al. |
| 2004/0129895 A1 | 7/2004 | Goldstein et al. |
| 2007/0181834 A1 | 8/2007 | Kleinschmidt |
| 2011/0242515 A1 | 10/2011 | Ceglio et al. |
| 2012/0182538 A1* | 7/2012 | Koole et al. .............. 355/75 |

* cited by examiner

ILLUMINATION SYSTEM WITH TIME MULTIPLEXED SOURCES FOR RETICLE INSPECTION

PRIORITY

The present application claims priority to the following United States Provisional Applications:

Ser. No. 61/612,640, entitled COMPACT FLY'S EYE ILLUMINATOR WITH SOURCE TIME MULTIPLEXING FOR EUV RETICLE INSPECTION, By Daimian Wang, filed Mar. 19, 2012;

Ser. No. 61/622,281, entitled COMPACT FLY'S EYE ILLUMINATOR WITH SOURCE TIME MULTIPLEXING FOR EUV RETICLE INSPECTION, By Daimian Wang, filed Apr. 10, 2012;

Ser. No. 61/652,722, entitled HIGH THROUGHPUT COMPACT FLYS EYE ILLUMINATOR WITH SOURCE TIME MULTIPLEXING FOR EUV RETICLE INSPECTION USING GRAZING INCIDENCE CONDENSOR AND PUPIL FACETS, By Daimian Wang, filed May 29, 2012; and Ser. No. 61/652,710, entitled HIGH THROUGHPUT COMPACT FLYS EYE ILLUMINATOR WITH SOURCE TIME MULTIPLEXING FOR EUV RETICLE INSPECTION USING GRAZING INCIDENCE HYBRID CONDENSOR/PUPIL FACET, By Daimian Wang et al., filed May 29, 2012.

TECHNICAL FIELD

The present disclosure generally relates to the field of illumination systems and more particularly to illumination systems for reticle inspection.

BACKGROUND

Some optical systems rely on ambient light from their surroundings to provide sufficient illumination for inspection, metrology, or any other type of sample analysis. Other optical systems require specialized illumination systems to project illumination within constraints such as, but not limited to, angle, area, wavelength, and/or intensity. Reticle inspection typically requires irradiance patterns directed at a reticle plane with specified numerical aperture and cone orientation. As such, Illumination systems for reticle inspection are among the most specialized illumination systems.

The extent of the irradiance pattern is also carefully controlled for reticle inspection, and irradiance uniformity at the reticle is among the most sensitive requirements. Present and past reticle inspection systems have relied upon a number of different illumination systems. However, extreme ultraviolet (EUV) reticle inspection presents problems that are not fulfilled by the current art. Some existing illumination systems utilize deep ultraviolet (DUV) wavelengths. Accordingly, the size and type of defects that can be detected and reviewed are limited.

Single source illumination systems are unable to provide illumination with sufficient brightness for EUV lithography, and multiple source illumination systems tend to exceed desired size restrictions and/or fail to provide the required uniformity. Various designs and concepts can be found in the following references: U.S. Pat. Nos. 6,396,068, 6,861,656, 7,183,565, US Patent Application No. 2007/0181834, and non-patent literature: Proc. OF SPIE Vol. 6517 56170J-1— Development of optics for EUV lithograph tools, published by NIKON Corporation. The foregoing are all incorporated by reference in their entirety as if fully set forth herein. In light of the foregoing systems and methods, there clearly exists a need for a cohesive and competitive illuminator layout that is compatible with plan-of-record optics design and also meets all known system throughput, footprint, cost, manufacturability, uniformity, size, and debris mitigation requirements.

SUMMARY

The present disclosure is directed to an illuminator layout that cures one or more deficiencies in the current state of the art.

In one aspect, the disclosure is directed to an illumination system for reticle inspection including a plurality of illumination sources configured to provide pulsed illumination. A multiplexing mirror system is configured to receive pulses of illumination from the plurality of illumination sources and further configured to direct the pulses of illumination along an illumination path to a plurality of field mirror facets. The field mirror facets are each configured to receive a portion of illumination from the illumination path and direct at least a portion of the illumination to a plurality of pupil mirror facets. The pupil mirror facets are each configured to receive a portion of illumination reflected from one or more of the field mirror facets and further configured to direct the portion of illumination along a delivery path to a reticle.

In another aspect, the disclosure is further directed to a reticle inspection system incorporating the illumination system. The reticle inspection system further includes at least one detector configured to receive illumination reflected by the reticle along a collection path. At least one computing system in communication with the detector is configured to locate a defect of the reticle utilizing information (e.g. a collected image) associated with the illumination received by the at least one detector.

In yet another aspect, the disclosure is directed to a method of providing illumination for reticle inspection. The method includes at least the steps of: providing pulses of illumination utilizing a plurality of illumination sources; directing the pulses of illumination along an illumination path utilizing a multiplexing mirror system; receiving portions of illumination from the illumination path utilizing a plurality of field mirror facets; receiving portions of illumination reflected from the plurality of field mirror facets utilizing a plurality of pupil mirror facets; and directing the portions of illumination received from the plurality of field mirror facets along a delivery path to a reticle. The method may be manifested by the illumination system and/or inspection system described herein. In some embodiments, however, one or more steps of the method may be implemented by additional or alternative means known to the art.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

FIGS. 1 through 7 generally illustrate a system and method of providing illumination for inspecting and/or imaging a reticle (sometimes referred as a "mask"). The illuminator layout described herein may enable EUV reticle inspection by utilizing two or more multiplexed illumination sources to provide illumination with sufficient brightness and uniformity. Some embodiments are further directed to a compact design for commercial advantages. Many of the systems and methods described herein may be extended to applications beyond EUV reticle inspection. Accordingly, the disclosure should be construed as expansively applying to any inspection system (e.g. wafer or mask inspection system) benefiting from brightness, uniformity, or any other technical or commercial advantages enabled by the following embodiments.

Figure 1:
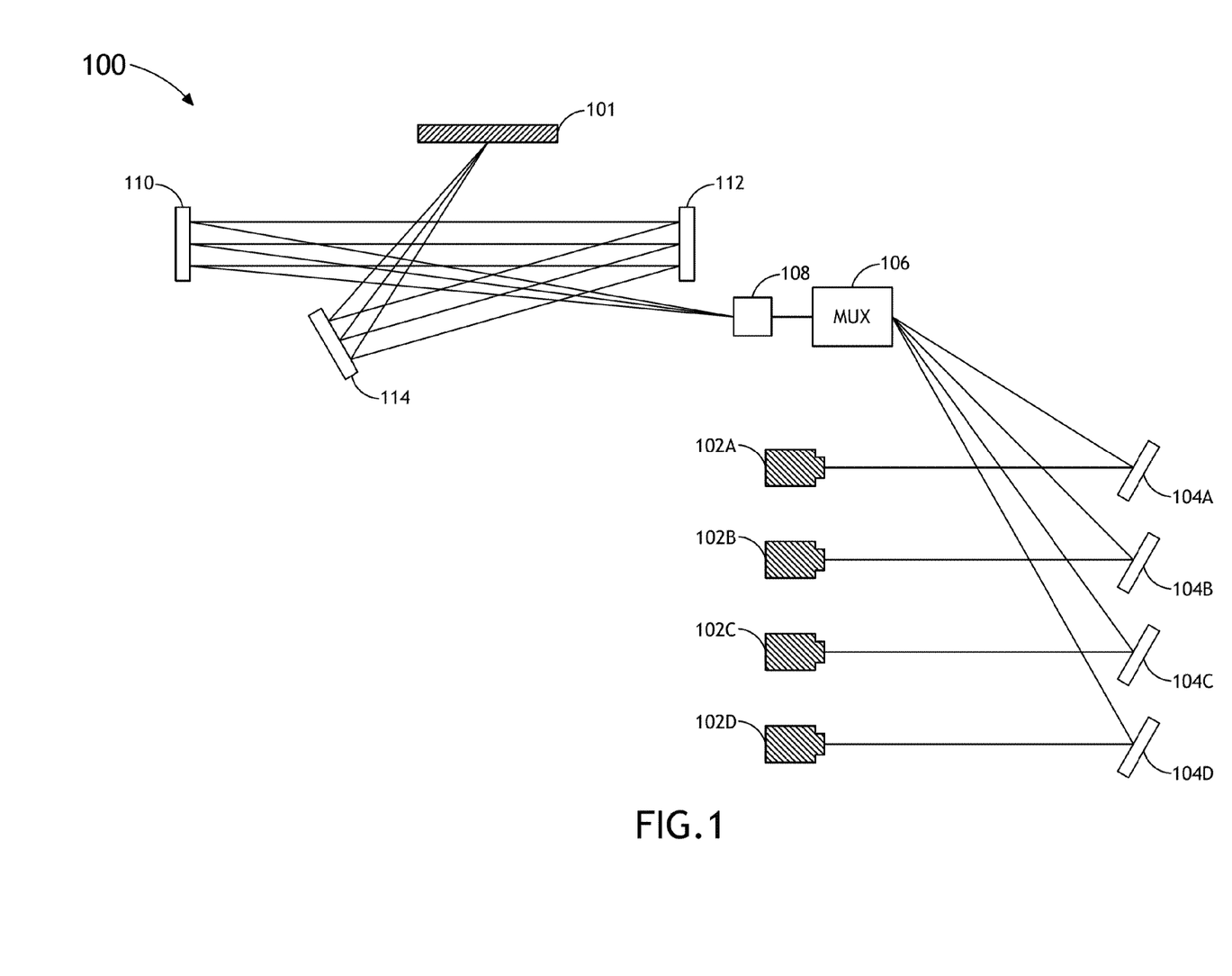
FIG. 1 illustrates an illumination system for reticle inspection, in accordance with an embodiment of this disclosure.

FIG. 1 illustrates an illuminator layout of a system 100 for inspecting a reticle 101 or any other sample. The illuminator includes a plurality of illumination sources 102 configured to provide pulsed illumination. In some embodiments, each of the illumination sources 102 is configured to provide illumination at one or more wavelengths in the EUV band (i.e. approximately 5 nm to 124 nm). The illumination sources 102 may be configured to provide pulses of illumination to a multiplexing mirror system 106 or any other illumination multiplexer. In some embodiments, the illuminator further includes a plurality of collector mirror facets 104 configured to receive the pulses of illumination from the illumination sources 102 and reflect the pulses of illumination to the multiplexing mirror system 106. For example, an ellipsoidal collector 104 may be disposed at a selected distance (e.g. approximately 0.57 meters) away from a corresponding illumination source 102. Directing illumination from the illumination sources 102 to the multiplexing mirror system 106 via the collector mirror facets 104 may allow disposition of the illumination sources 102 at one or more selected locations in close proximity to one another for easy access and space-saving design.

The multiplexing mirror system 106 is configured to direct each individual pulse received from each of the illumination sources 102 along a common illumination path so that illumination is provided by the plurality of illumination sources 102 along the illumination path, as if being provided by a single illumination source. By combining illumination from the plurality of illumination sources 102, the multiplexing mirror system 106 is enabled to provide illumination with sufficient brightness along the illumination path. The multiplexing mirror system 106 may include a plurality of mirror facets coupled to at least one actuator, such as a motor or servo. The actuator may be configured to actuate the mirror facets to receive each pulse of illumination with a mirror facet oriented at a selected angle of incidence so that the pulses of illumination are directed along a common axis of the illumination path. In some embodiments, the multiplexing mirror system 106 includes a rotatable polygon mirror with a plurality of mirror facets that have similar or substantially identical sizes and optical properties.

The illuminator may further include a plurality of field mirror facets 110 and a plurality of pupil mirror facets 112. Each of the field mirror facets may be configured to receive a portion of illumination from the illumination path and direct the portion of illumination to at least one corresponding pupil mirror facet 112. The pupil mirror facets 112 may be configured to direct the illumination received from the field mirror facets 110 along a delivery path to the reticle 101. In some embodiments, the delivery path includes a condenser 114 configured to converge illumination received from the pupil mirror facets 112 and direct the converged illumination to a portion of the reticle 101 for inspection. In some embodiments, the field mirror facets 110 include a plurality of spherical mirror facets and the pupil mirror facets 112 include a plurality of planar mirror facets to facilitate simpler fabrication. In some embodiments, a relatively small angle of incidence (e.g. approximately 10 degrees or less) enables the use of spherical facets. In other embodiments, however, the field mirror facets 110 and/or the pupil mirror facets 112 may include alternative surface geometries, such as conical mirror facets.

The illuminator may further include an intermediate focus aperture 108 configured to focus illumination flowing along the illumination path through the aperture 108 by removing stray illumination and improving stability. The aperture 108 may be disposed between the multiplexing mirror system 106 and the field mirror facets 110. In some embodiments, the aperture 108 is further configured to block particles emitted by the illumination sources 102 from travelling to the field mirror facets 110, the pupil mirror facets 112, condenser 114, and/or the reticle 101. For example, the aperture 108 may have a selected dimensional characteristic (e.g. approximately 4 mm or less in diameter) enabling a sufficient level of particle isolation. In some embodiments, the aperture 108 is further configured to limit gas flow along the illumination path enabling it to function as a differential pumping aperture.

In some embodiments, illumination is directed from the intermediate focus aperture 108 between the pupil mirror facets 112 and the condenser 114 to the field mirror facets 110. The illumination may be folded by the field mirror facets 110 with a small angle of incidence to use the space between the reticle 101 and an objective assembly. Alternatively, illumination from the aperture 108 may be directed below the condenser for various layout purposes. The angle of incidence on the field mirror facets 110 may be relatively small to improve mirror reflectivity since the reflectivity of near-normal incidence multi-layer mirrors tends to decrease as angle of incidence increases. Furthermore, a smaller angle of incidence may enable the use of spherical field mirror facets which are generally easier to manufacture and may have alignment advantages over conic mirrors.

In an exemplary embodiment, the pupil mirror facets 112 may be disposed at least 40 mm below the reticle plane to leave enough space for a particle blocking mechanism associated with the reticle 101. The condenser 114 may include an ellipsoidal mirror disposed less than 120 mm below the reticle plane to leave enough space for the objective mirror assembly. In some embodiments, all mirrors are disposed below the reticle plane to leave enough space for a stage configured to support the reticle 101. The stage may be further configured to actuate the reticle 101 to image and/or inspect a selected portion of the reticle 101. In some embodiments, the optics footprint is approximately 4 m horizontally by 1.67 m vertically allowing for substantial cost effectiveness, among other commercial and technical advantages.

The foregoing example is included to illustrate potential advantages associated with at least one embodiment of the system 100 and should not be construed as limiting the disclosure in any way. Several variations to the system 100 may be made without deviating from the scope of this disclosure. For example, the reticle 101 may be disposed with a patterned surface (to be inspected) facing upwards or sideways, rather than downwards. For further example, the illuminator plane may rotate any angle around the axis of the chief ray of illumination travelling from the condenser 114 to the reticle 101.

Figure 2A:
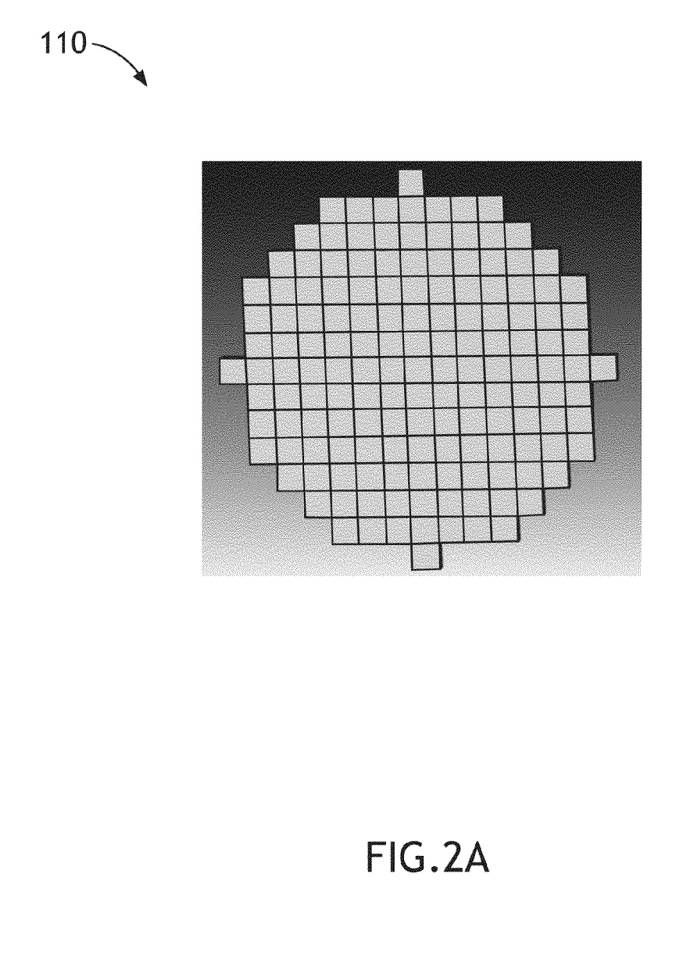
FIG. 2A illustrates a plurality of mirror facets disposed according to a fly's eye optical arrangement, in accordance with an embodiment of this disclosure.

In some embodiments, the field mirror facets 110 and the pupil mirror facets 112 are arranged according to a fly's eye mirror configuration, as illustrated in FIG. 2A. In some embodiments, the tip and tilt angles of each pupil mirror facet 112 enable illumination reflected from each of the field mirror facets 110 to overlap onto the reticle 101. The facet surfaces may include any geometric shape (e.g. pentagon, hexagon, circle) and are not limited to the rectangular surfaces illustrated in FIG. 2A. In some embodiments, the facets are disposed in close proximity to one another to effectively utilize spatial parameters of the pupil plane.

Due to instability of illumination source position and far field distribution, the illumination may suffer from pupil instability, field profile instability, and/or non-uniformity. However, the pupil mirror facets 112 and field mirror facets 110 may be configured to improve the pupil stability, field stability, and uniformity by forming multiple pupil images and overlapping field images. Each field mirror facet 110 may be configured to image an intermediate field to the pupil plane defined by the plurality of pupil mirror facets 112. In turn, each pupil mirror facet 112 may be configured to image a corresponding field mirror facet 110 to the illuminator field so that images corresponding to the plurality of field mirror facets 110 are overlapped at the reticle 101.

Figure 2B:
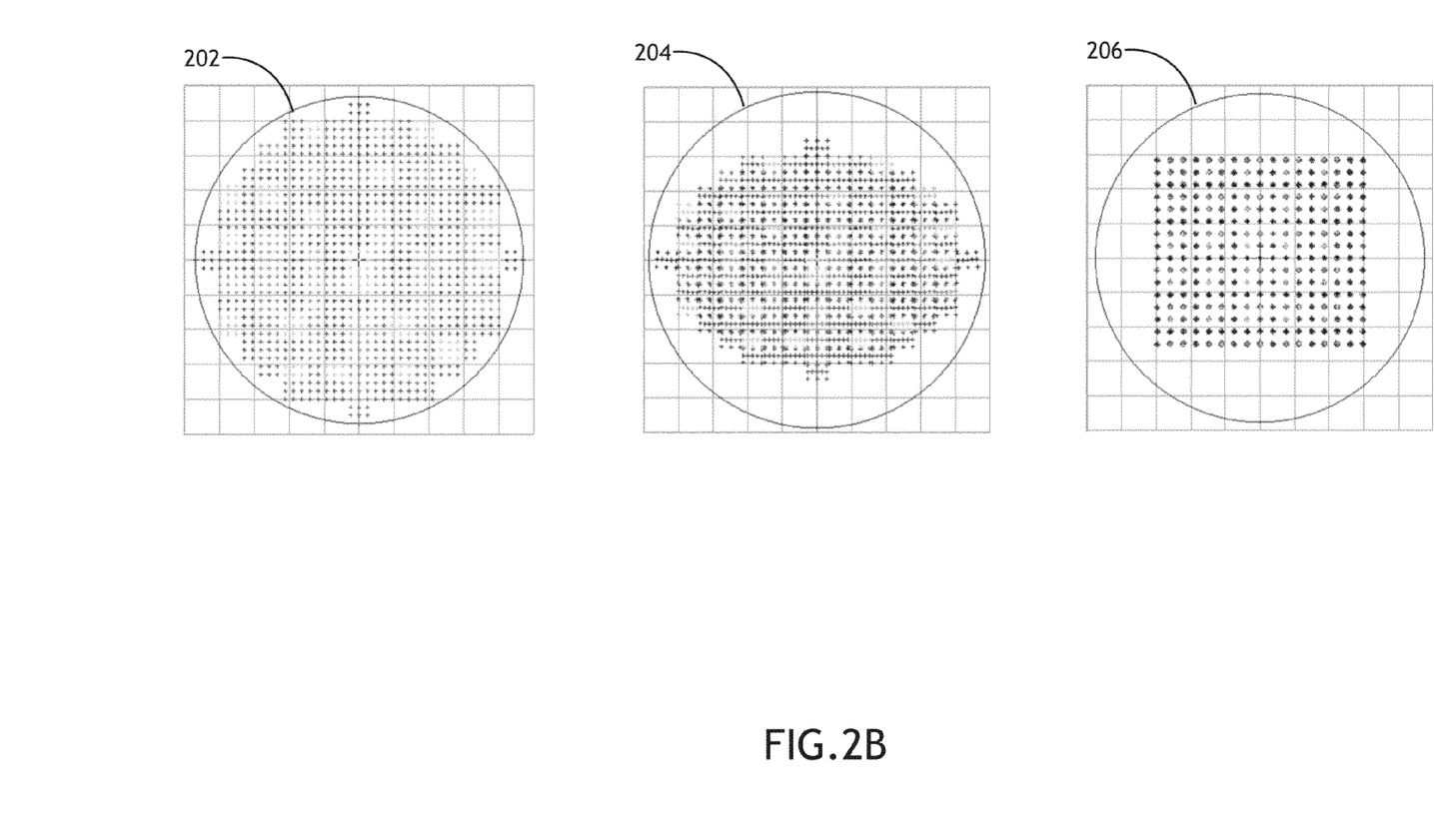
FIG. 2B illustrates illumination footprints on a pupil plane, a field plane, and an intermediate focus plane, in accordance with an embodiment of this disclosure.

FIG. 2B depicts illumination footprints 202, 204, and 206 respectively associated with an exemplary embodiment of the pupil plane, the field plane, and the intermediate focus plane. In the exemplary embodiment, the pupil plane may be defined by a total of 149 pupil mirror facets 112, 15 facets being disposed along the diameter of the pupil 112, the pupil field assembly being approximately 26.3 mm in diameter. The field plane may be defined by the plurality field mirror facets 110 selected to be conjugate with an exemplary rectangular field shape, the field facet assembly being approximately 70 mm in diameter. The intermediate focus plane may be defined by the intermediate focus (IF) aperture 108. The IF footprint 206 illustrates the overlapped illumination resulting from interaction with the field mirror facets 110 and the pupil mirror facets 112. The overlapping enables the reticle 101 to receive substantially uniform illumination as a result of intensity averaging from reflected illumination from the field mirror facets 110. In the exemplary embodiment, the illumination footprint 206 at the IF plane is approximately 2.5 mm by 2.5 mm. It is noted herein that the foregoing dimensions are illustrative of at least one exemplary embodiment, but are not in any way intended as limitations of this disclosure.

The collector mirror facets 104, field mirror facets 110, pupil mirror facets 112, and condenser 114 may include near-normal incidence mirror facets (e.g. Mo/Si multilayer mirror surfaces). In some embodiments, however, one or more of the foregoing components are replaced with grazing incidence mirror facets. Some of the following embodiments illustrate variations on the illuminator layout illustrated in FIG. 1 where grazing incidence mirror facets are implemented in one or more portions of the illuminator layout.

Figure 3A:
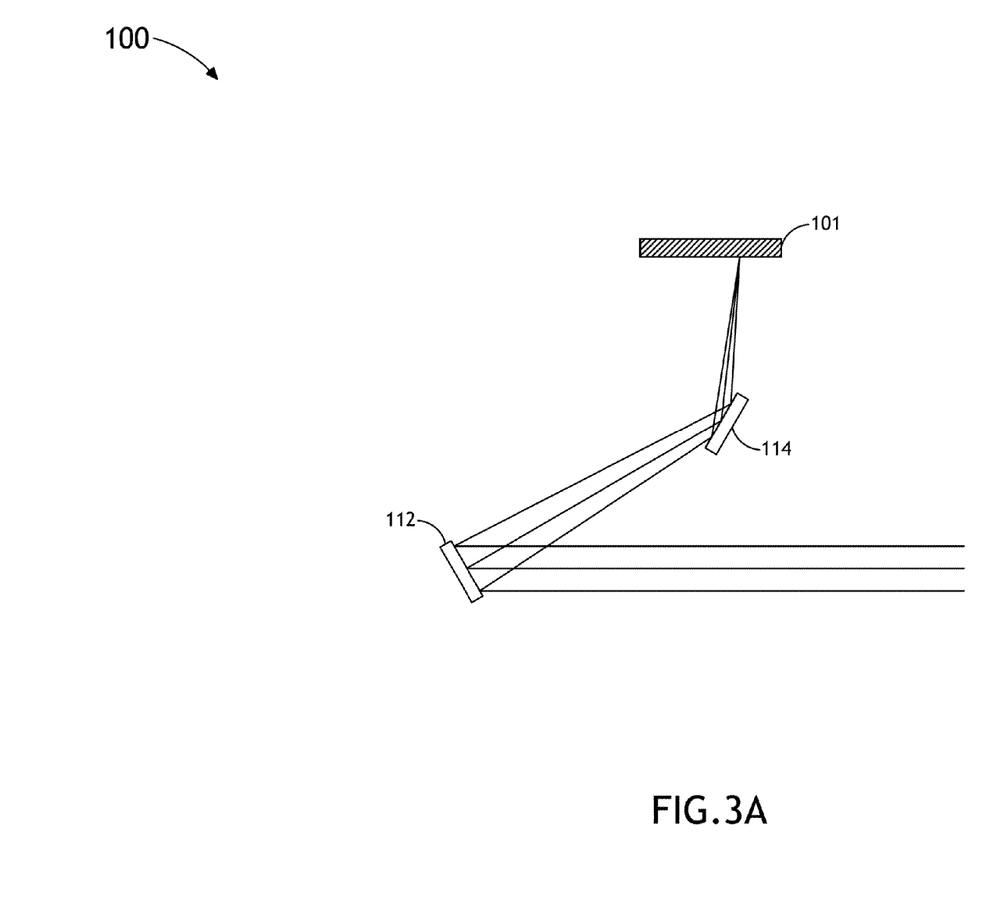
FIG. 3A illustrates a portion of the illumination system including a grazing incidence condenser, in accordance with an embodiment of this disclosure.
Figure 3B:
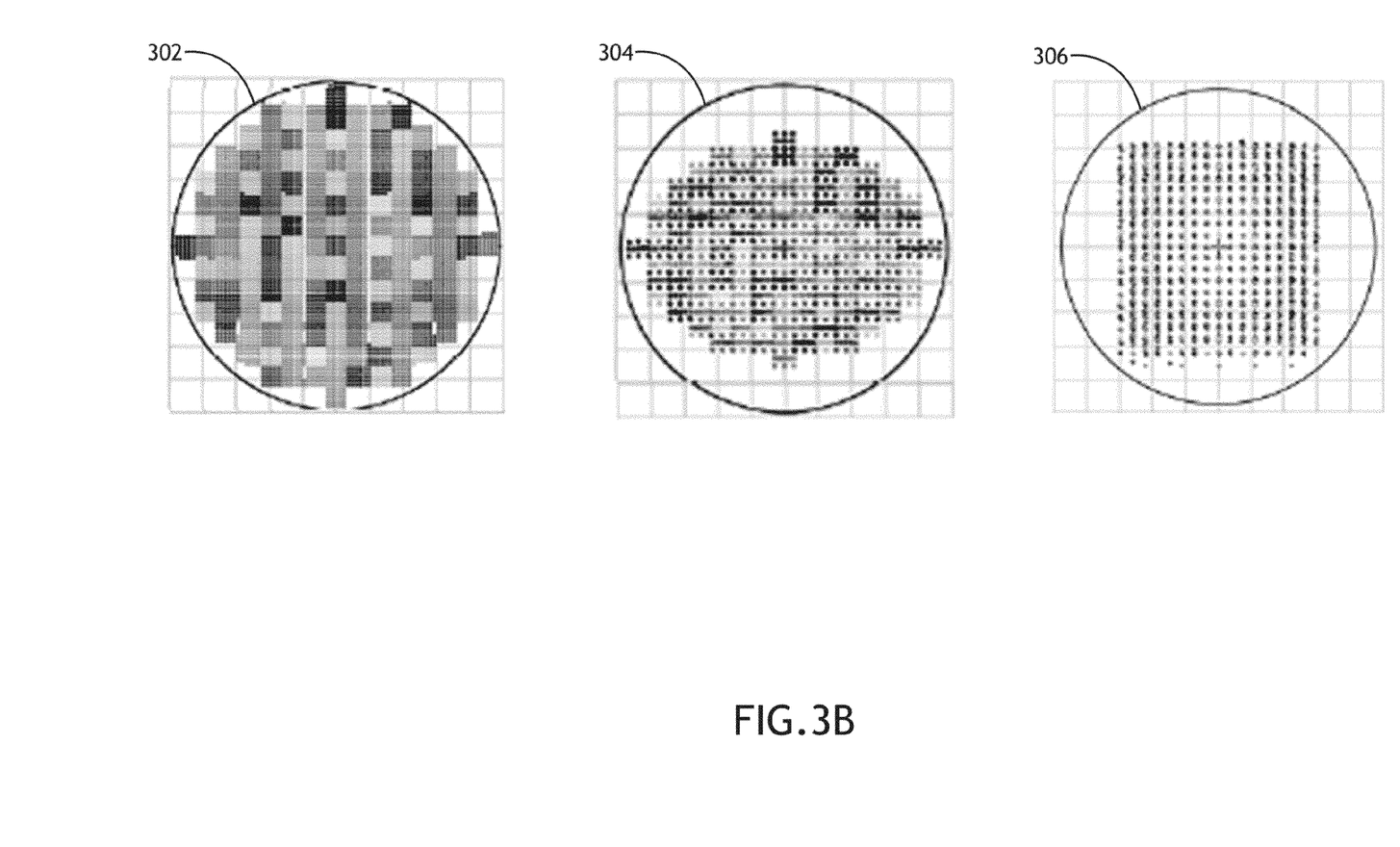
FIG. 3B illustrates illumination footprints on a pupil plane, a field plane, and an intermediate focus plane, wherein the illumination system includes a grazing incidence condenser, in accordance with an embodiment of this disclosure.
Figure 3C:
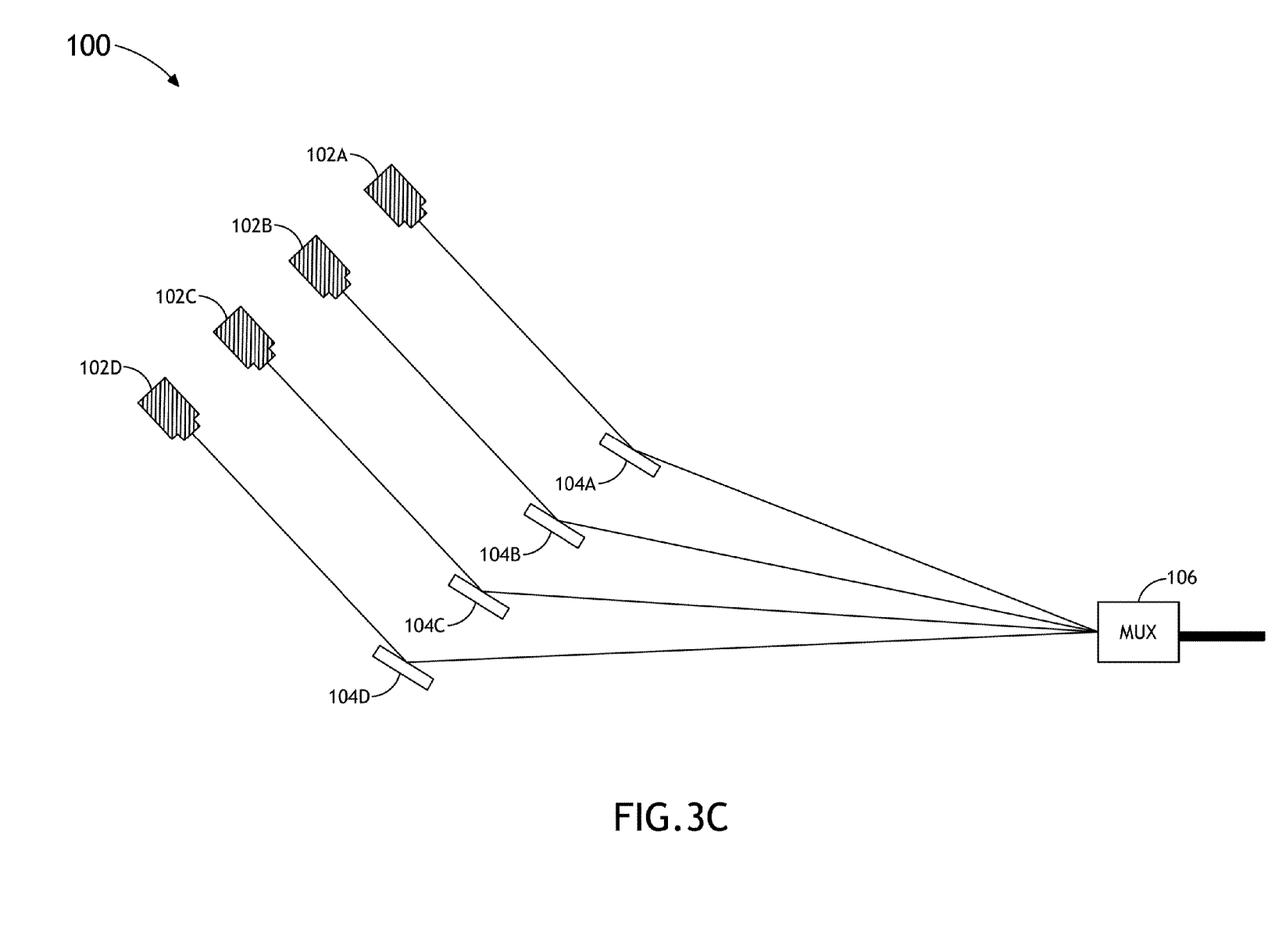
FIG. 3C illustrates a portion of the illumination system including grazing incidence collector mirror facets, in accordance with an embodiment of this disclosure.

FIG. 3A illustrates an embodiment of the system 100 where the illuminator includes a grazing incidence condenser 114. The grazing incidence condenser 114 may allow for increased throughput in comparison with a normal incidence condenser 114 (as in FIG. 1). For example, the grazing incidence condenser 114 may allow for approximately 20% or more increased illumination throughput. FIG. 3B depicts illumination footprints 302, 304, and 306 respectively associated with an exemplary embodiment of the pupil plane, the field plane, and the intermediate focus plane according to the modified system 100 illustrated in FIG. 3A. In some embodiments, illustrated in FIG. 3C, the illuminator may further include grazing incidence collector mirror facets 104 for higher reflectivity (e.g. approximately 20% higher).

Figure 4A:
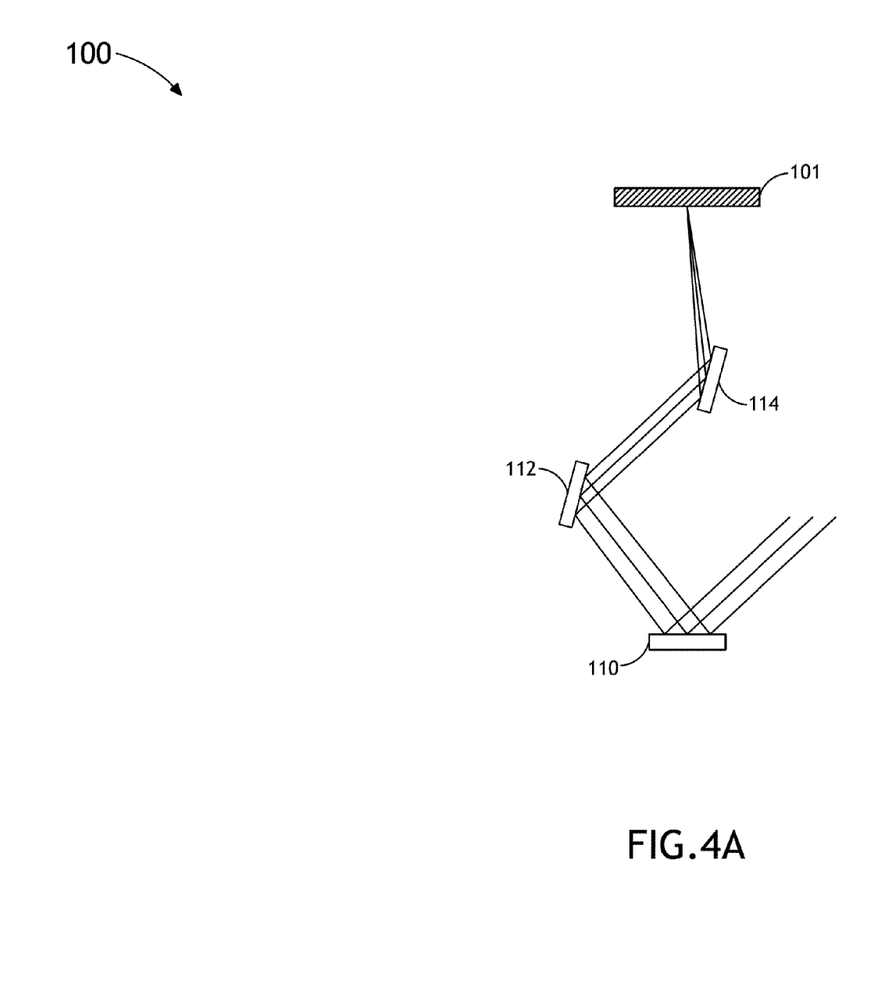
FIG. 4A illustrates a portion of the illumination system including grazing incidence pupil mirror facets and a grazing incidence condenser, in accordance with an embodiment of this disclosure.

FIG. 4A illustrates another embodiment of the system 100 where the illuminator includes a grazing incidence condenser 114 and grazing incidence pupil mirror facets 112. Utilizing a combination of the grazing incidence condenser 114 and the grazing incidence pupil mirror facets 112 may substantially increase illumination throughput (e.g. approximately 70% higher than near-normal incidence condenser and pupil facets). In some embodiments, the pupil mirror facets 112 are disposed within the focal plane of the condenser 114 to reduce telecentric error. Due to the large aberration of the grazing incidence ellipsoidal condenser mirror, the pupil mirror facets 112 may need to be tilted and disposed nearly parallel to the condenser 114 so that each of the pupil mirror facets 112 is within the focal plane of each portion of the condenser 114.

Figure 4B:
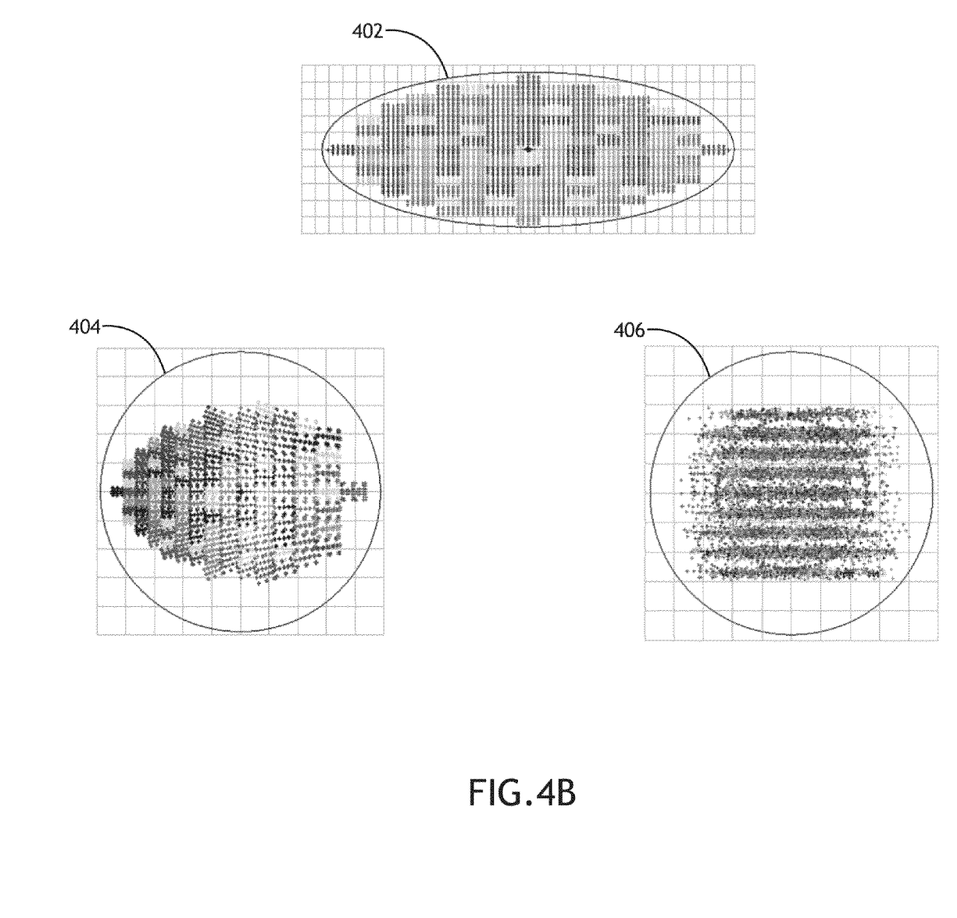
FIG. 4B illustrates illumination footprints on a pupil plane, a field plane, and an intermediate focus plane, wherein the illumination system includes grazing incidence pupil mirror facets and a grazing incidence condenser, in accordance with an embodiment of this disclosure.

FIG. 4B depicts illumination footprints 402, 404, and 406 respectively associated with an exemplary embodiment of the pupil plane, the field plane, and the intermediate focus plane according to the modified system 100 illustrated in FIG. 4A. In the exemplary embodiment, the footprint 402 associated with each pupil mirror facet 112 shows an aspect ratio of approximately 6.5 to 1 as a result of grazing incidence on the pupil mirror facets 112. In some embodiments, the pupil mirror facets 112 may include hyperboloid surfaces with foci overlapping with foci of the ellipsoidal condenser 114 to reduce aberration in the image of the field mirror facets 110 on the reticle plane.

Figure 5A:
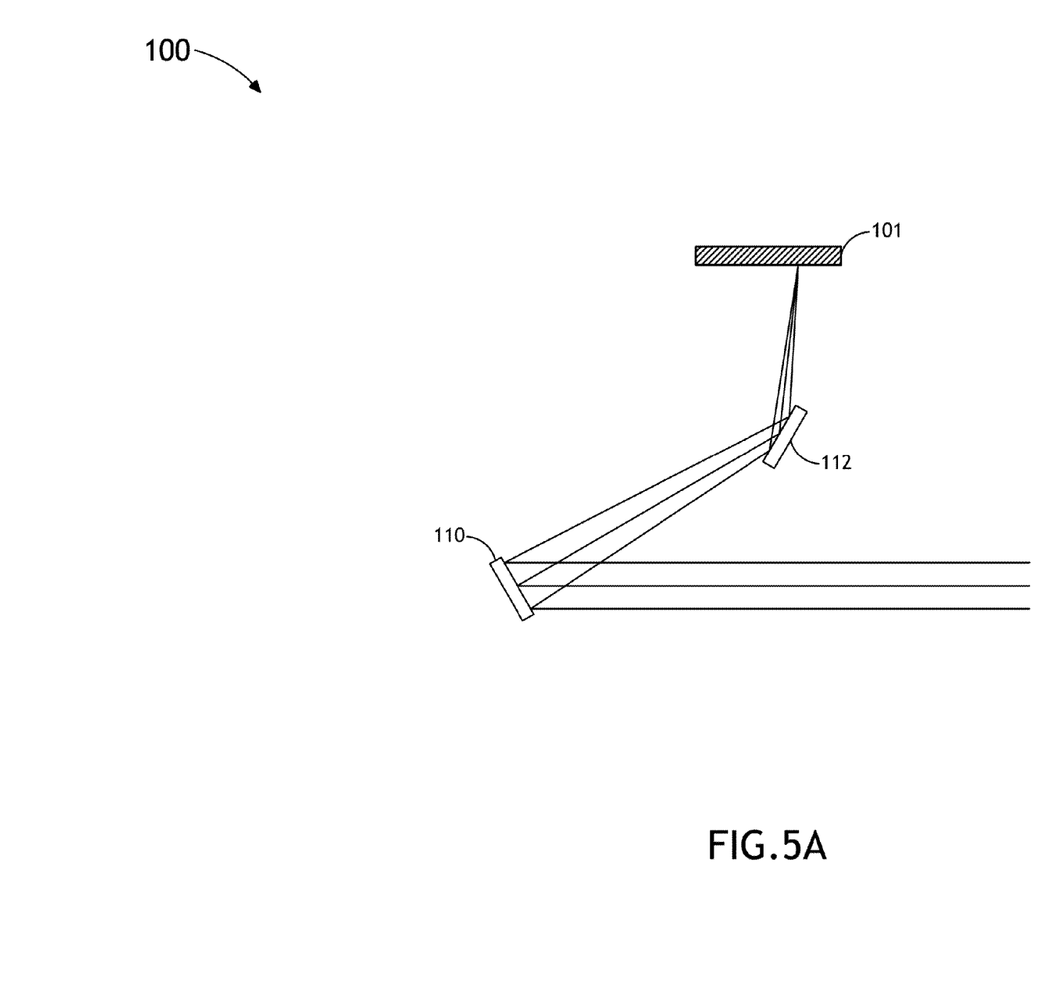
FIG. 5A illustrates a portion of the illumination system including grazing incidence pupil mirror facets functioning as a grazing incidence condenser, in accordance with an embodiment of this disclosure.

FIG. 5A illustrates another embodiment of the system 100 where the illuminator includes grazing incidence pupil mirror facets 112 configured to function as a condenser (i.e. hybrid pupil/condenser). In some embodiments, conic field mirror facets 110 are utilized to reduce aberration on the pupil mirror facets 112. Each of the field mirror facets 110 is imaged by a corresponding one of the pupil mirror facets 112 onto the reticle 101. The pupil mirror facets 112 are configured to overlap images of the field mirror facets 110 onto the reticle with grazing incidence for increased reflectivity. Illumination throughput may be further increased (e.g. approximately 45% higher illumination throughput) because a condenser is not required between the pupil mirror facets 112 and the reticle 101.

Figure 5B:
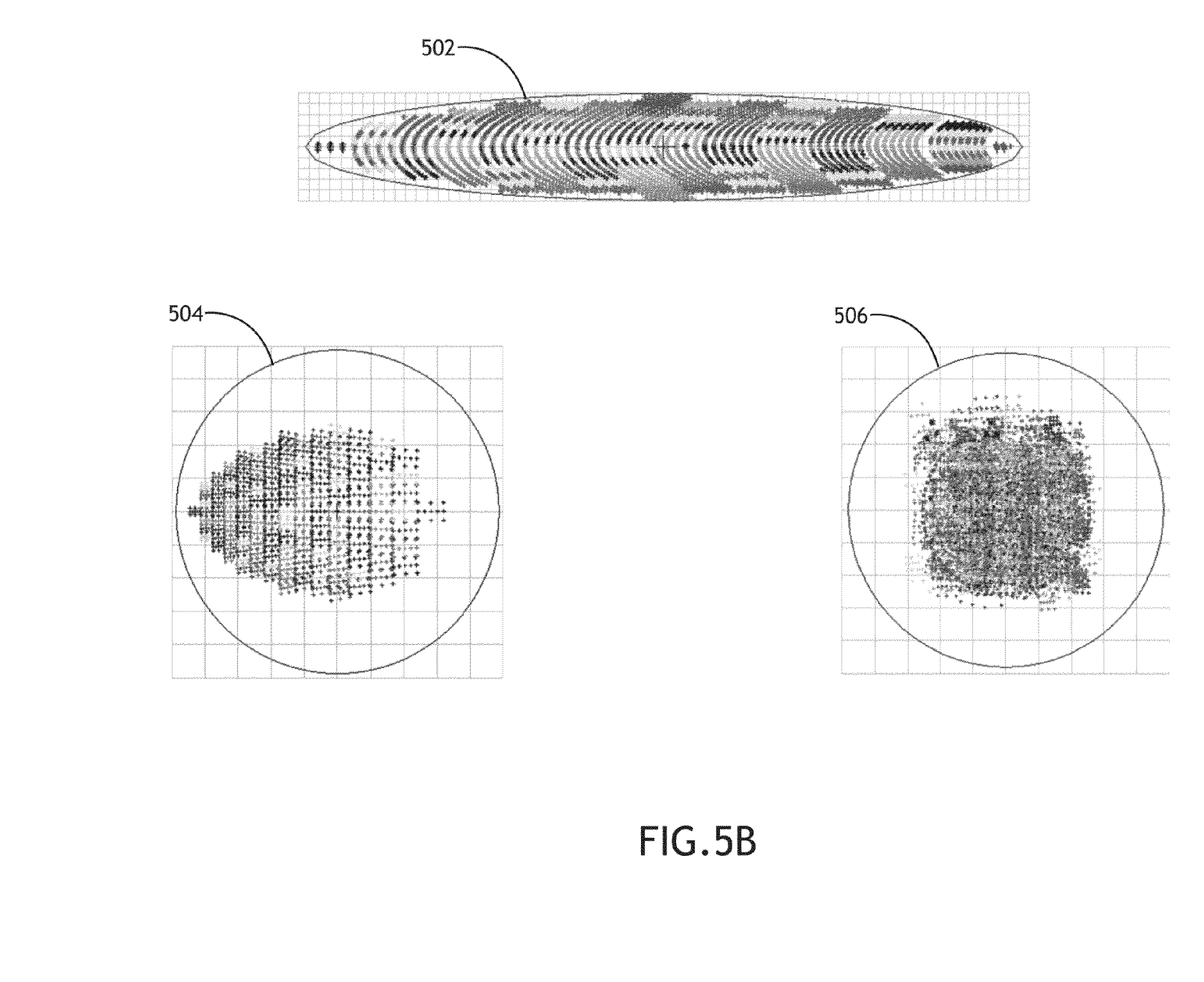
FIG. 5B illustrates illumination footprints on a pupil plane, a field plane, and an intermediate focus plane, wherein the illumination system includes grazing incidence pupil mirror facets functioning as a grazing incidence condenser, in accordance with an embodiment of this disclosure.

FIG. 5B depicts illumination footprints 502, 504, and 506 respectively associated with an exemplary embodiment of the pupil plane, the field plane, and the intermediate focus plane according to the modified system 100 illustrated in FIG. 5A. In the exemplary embodiment, the footprint 502 associated with each pupil mirror facet 112 shows an aspect ratio of approximately 4 to 1 as a result of grazing incidence on the pupil mirror facets 112. In some embodiments, the IF aperture 108 may be imaged near the pupil mirror facets 112 instead of being imaged on the pupil mirror facets 112 to reduce telecentric error, but may result in decreased illumination due to overlapping on the pupil mirror facets 112.

Figure 6:
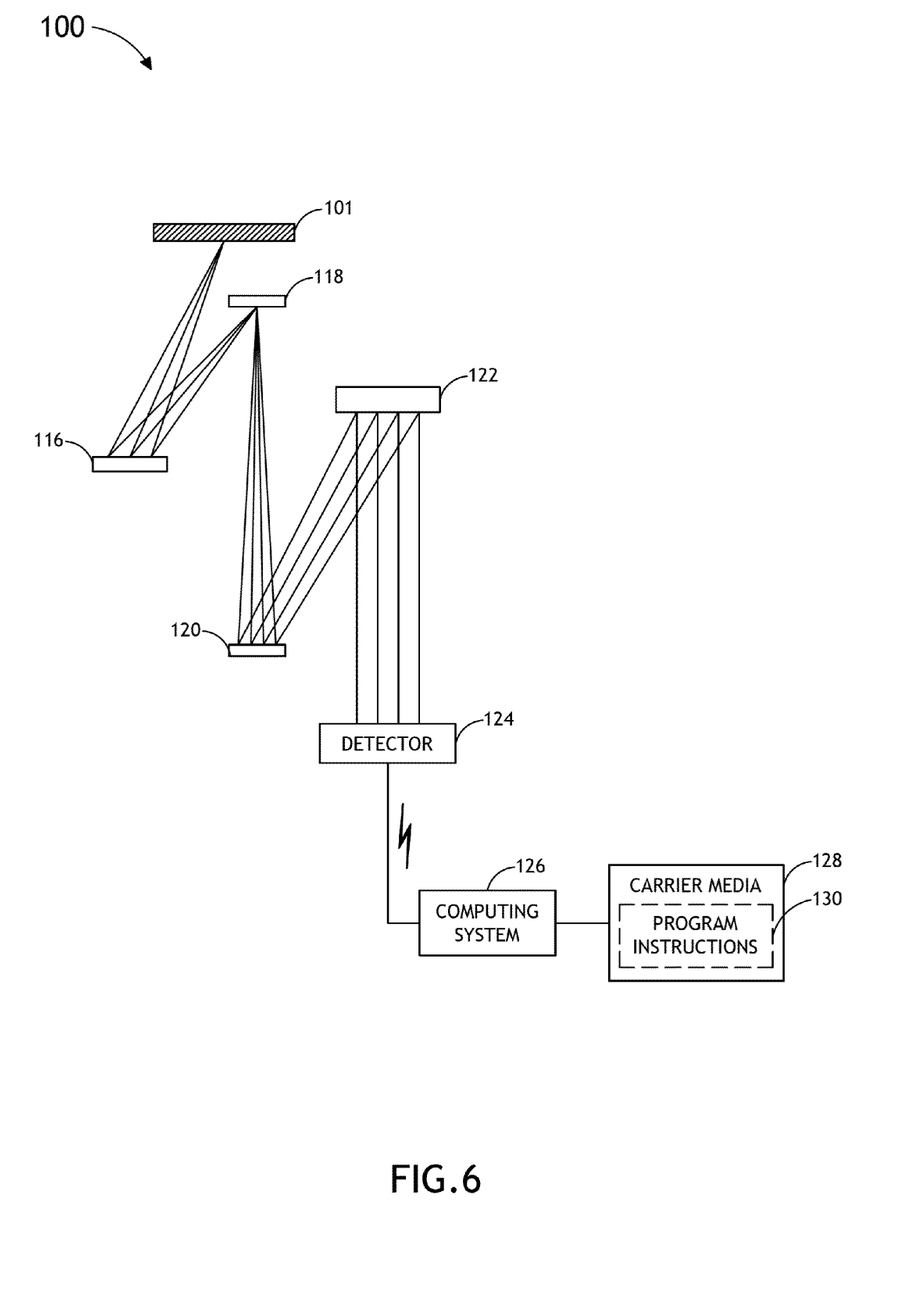
FIG. 6 illustrates collection path of an inspection incorporating the illumination system, wherein the collection path includes 4 near normal-incidence mirrors, in accordance with an embodiment of this disclosure.

FIG. 6 illustrates projection optics of the inspection system 100 configured to direct illumination reflected from the illuminated portion of the reticle 101 along a collection path to a detector 124, such as a time delay integration (TDI) camera or TDI photo-detector array. In some embodiments, the projection optics include at least a first mirror 116, a second mirror 118, a third mirror 120, and a fourth mirror 122 defining the collection path to the detector 124. In some embodiments, the stage for supporting and/or actuating the reticle is disposed above the reticle plane; accordingly, the mirrors may be disposed below the reticle 101. In some embodiments, the pupil mirror facets 112 and the condenser 114 may be disposed at different sides of the optical path from the reticle 101 to the first mirror 116. The foregoing arrangement may allow the pupil mirror facets 112 to be disposed within the focal plane of the condenser 114 thereby improving telecentricity of the illuminator without affecting illumination flowing from the reticle 101 to the first mirror 116.

At least one computing system 126 may be communicatively coupled to the detector 124. The computing system 126 may include, but is not limited to, a personal computing system, mainframe computing system, workstation, image computer, parallel processor, or any processing device known in the art. In general, the term "computing system" may be broadly defined to encompass any device having one or more processors configured to execute program instructions 130 from at least one carrier medium 128.

The computing system 126 may be configured to receive information (e.g. image frames, pixels, intensity measurements) associated with illumination collected by the detector 124. The computing system 126 may be further configured to carry out various inspection, imaging, and/or sample analysis algorithms known to the art utilizing the collected information. For example, the computing system 126 may be configured to locate one or more defects of the reticle 101 and/or generate review images associated with the one or more defects. In some embodiments, the computing system 126 may be further configured to characterize the one or more defects (e.g. brightfield or darkfield defect, spatial property of defect). In some embodiments, the one or more computing systems 126 may be further configured to execute or control execution of various steps or functions described herein. For example, the one or more computing systems 126 may be configured to control the pulse rate of the illumination sources 102 or to drive one or more actuators (e.g. multiplexing mirror actuator or stage actuator) of the system 100.

Figure 7:
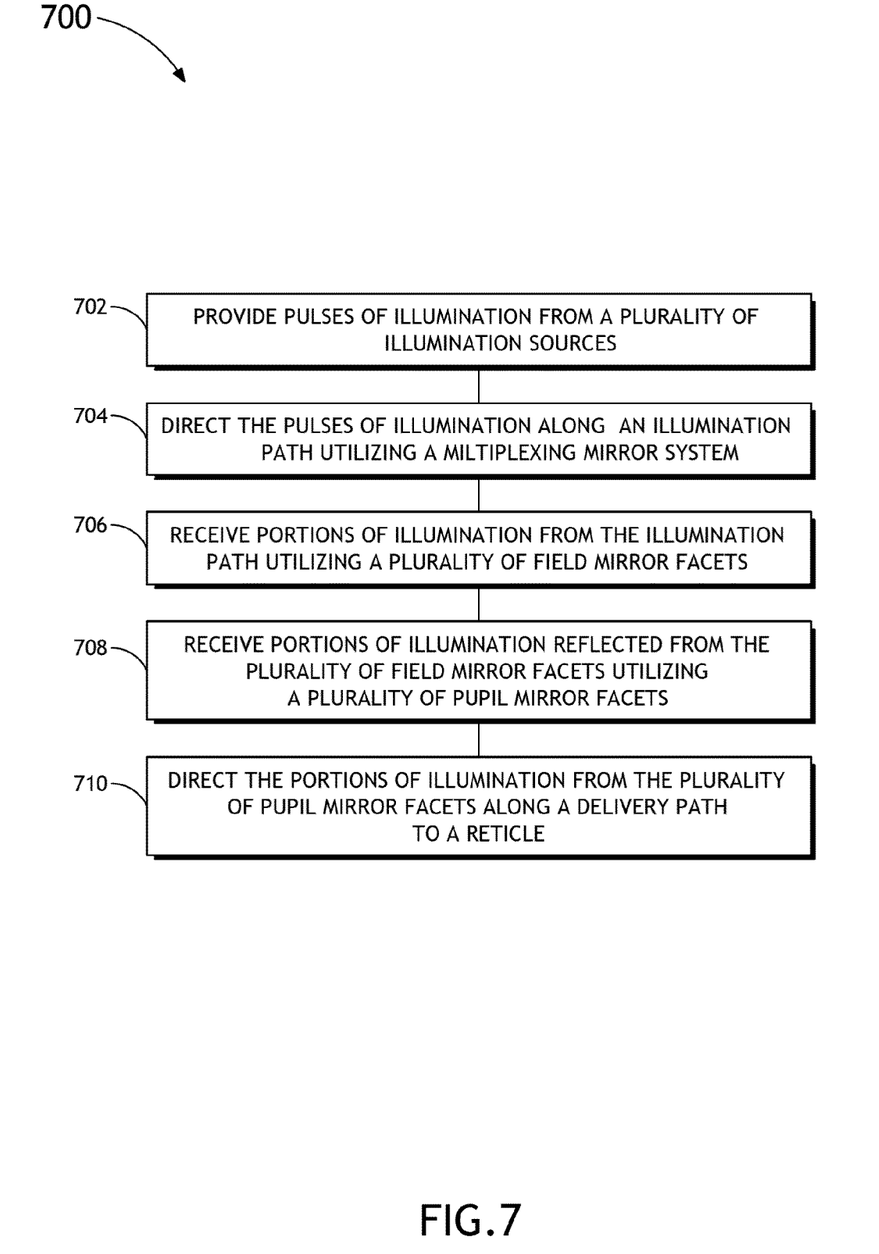
FIG. 7 is a flow diagram illustrating a method of providing illumination for reticle inspection, in accordance with an embodiment of this disclosure.

FIG. 7 is a flow chart illustrating a method 700 of providing illumination for reticle inspection in accordance with system 100. However, one or more steps of method 700 may be accomplished utilizing variations of the illuminator of system 100. Accordingly, method 700 is intended to encompass any means known to the art for carrying out the steps that follow.

At step 702, pulses of illumination are provided by a plurality of illumination sources 102. In some embodiments, at least two illumination sources 102 providing illumination in the EUV band are utilized to provide sufficiently bright illumination for EUV reticle inspection. In some embodiments, such as those including near-normal incidence pupil mirror facets 112 and condenser 114, at least four illumination sources 102 may be required to provide sufficiently bright illumination for EUV reticle inspection.

At step 704, the pulses of illumination are received by a multiplexing mirror system 106 from the illumination sources 102 via a collector assembly 104. The multiplexing mirror system 106 may direct the pulses of illumination along a common illumination path such that the pulses of illumination coming from the multiplexed sources 102 are as if coming from a single illumination source.

At step 706, the substantially continuous illumination is directed along the illumination path to a plurality of field mirror facets 110. At step 708, the field mirror facets 110 may reflect at least a portion of the illumination to a pupil plane defined by a plurality of pupil mirror facets 112. In some embodiments, the field mirror facets 110 and the pupil mirror facets 112 are arranged according to a fly's eye configuration so that the field images are overlapped by the pupil mirror facets 112.

At step 710, the (overlapped) illumination is directed from the pupil mirror facets 112 along a delivery path to the reticle 101 for imaging and/or inspection. In some embodiments, the delivery path further includes a condenser 114 for converging from the pupil mirror facets 112 and directing the converged illumination at the portion of the reticle 101 being illuminated (and inspected). In other embodiments, the pupil mirror facets 112 function as the condenser 114 (i.e. hybrid pupil/condenser) to converge the illumination received from the field mirror facets 110 and direct the converged illumination at the reticle 101.

Method 700 may further include one or more steps for carrying out a function described with regard to foregoing embodiments of system 100. As such, the foregoing steps are illustrative of an embodiment of the method and should not be construed as limitations. Those having skill in the art will further appreciate that there are various vehicles by which processes, systems and/or other technologies described herein can be effected (e.g. various combinations of hardware, software, and/or firmware). The preferred vehicle will vary with the context of implementation.

Program instructions implementing steps or functions, such as those described herein, may be transmitted over or stored on carrier media. In some embodiments, a carrier medium may include a transmission medium such as a wire, cable, or wireless transmission link. In some embodiments, the carrier medium may include a storage medium such as a read-only memory, a random access memory, a magnetic or optical disk, or a magnetic tape.

Some of the steps or functions described herein require storage of results by a storage medium. The results may include any collected or determined information described herein and may be stored in any manner known in the art. After the results have been stored, the results may be accessed from the storage medium and utilized for any of the method or system embodiments described herein, formatted for display to a user, used by another software module, method, or system, etc. Furthermore, the results may be stored permanently, semi-permanently, or temporarily (i.e. for a specified or indefinite period of time). For example, the storage medium may be random access memory (RAM), and the results may not necessarily persist indefinitely in the storage medium.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed is:

1. An illumination system for reticle inspection, comprising:
    a plurality of illumination sources, wherein at least one of the illumination sources is an extreme ultraviolet (EUV) illumination source;
    a multiplexing mirror system configured to at least receive pulses of EUV illumination from the plurality illumination sources, and further configured to direct the pulses of EUV illumination along an illumination path;
    a plurality of field mirror facets, at least some of the field mirror facets configured to receive a portion of EUV illumination from the illumination path; and
    a plurality of pupil mirror facets, at least some of the pupil mirror facets configured to receive a portion of EUV illumination reflected from the plurality of field mirror facets, and further configured to direct the portion of EUV illumination received from the plurality of field mirror facets along a delivery path to a reticle.

2. The system of claim 1, wherein the plurality of illumination sources are configured to provide illumination at one or more wavelengths in the range of approximately 5 nm to 124 nm.

3. The system of claim 1, wherein the multiplexing mirror system includes a plurality of actuatable mirror facets, wherein the multiplexing mirror system is configured to receive each pulse of EUV illumination utilizing a mirror facet with a selected angle of incidence.

4. The system of claim 3, wherein the plurality of actuatable mirror facets includes a rotatable polygon mirror.

5. The system of claim 1, wherein the plurality of pupil mirror facets are configured to direct overlapped portions of EUV illumination received from the plurality of field mirror facets along the delivery path to the reticle.

6. The system of claim 1, wherein the plurality of field mirror facets includes at least one of a plurality of spherical mirror facets and a plurality of conical mirror facets.

7. The system of claim 1, wherein the plurality of pupil mirror facets includes at least one of a plurality of planar mirror facets and a plurality of conical mirror facets.

8. The system of claim 1, further comprising:
    an aperture disposed along the illumination path, the aperture configured to allow at least a portion of EUV illumination from the plurality of illumination sources to flow through the aperture along the illumination path, and further configured to block particles emitted by the plurality of illumination sources from flowing along at least a portion of the illumination path.

9. The system of claim 1, further comprising:
    a plurality of collector mirror facets configured to receive the pulses of EUV illumination from the plurality of illumination sources, and further configured to direct the pulses of illumination to the multiplexing mirror system.

10. The system of claim 9, wherein the plurality of collector mirror facets includes at least one of a plurality of near normal incidence mirror facets and a plurality of grazing incidence mirror facets.

11. The system of claim 1, further comprising:
    a condenser disposed along the delivery path, the condenser configured to converge portions of EUV illumination received from the plurality of pupil mirror facets, and further configured to illuminate the reticle with the converged portions of EUV illumination.

12. The system of claim 11, wherein the condenser includes a grazing incidence mirror.

13. The system of claim 1, wherein the plurality of pupil mirror facets are configured to converge portions of EUV illumination received from the plurality of field mirror facets, and further configured to illuminate the reticle with the converged portions of EUV illumination.

14. The system of claim 13, wherein the plurality of pupil mirror facets includes a plurality of grazing incidence mirror facets.

15. A method of providing illumination for reticle inspection, comprising:
    providing pulses of extreme ultraviolet (EUV) illumination;
    directing the pulses of EUV illumination along an illumination path utilizing a multiplexing mirror system;
    receiving portions of EUV illumination from the illumination path utilizing a plurality of field mirror facets;
    receiving portions of EUV illumination reflected from the plurality of field mirror facets utilizing a plurality of pupil mirror facets; and
    directing the portions of EUV illumination from the plurality of pupil mirror facets along a delivery path to a reticle.

16. The method of claim 15, wherein the pulses of EUV illumination include illumination at one or more wavelengths in the range of approximately 5 nm to 124 nm.

17. The method of claim 15, further comprising:
    receiving at least one pulse of illumination utilizing a mirror facet of the multiplexing mirror system with a selected angle of incidence.

18. The method of claim 15, further comprising:
    overlapping portions of EUV illumination received from the plurality of field mirror facets utilizing the plurality of pupil mirror facets; and
    directing the overlapped portions of EUV illumination along the delivery path to the reticle.

19. The method of claim 15, further comprising:
    allowing at least a portion of EUV illumination from the plurality of illumination sources to flow through an aperture disposed along the illumination path; and
    blocking particles emitted by the plurality of illumination sources from flowing along at least a portion of the illumination path utilizing the aperture.

20. The method of claim 15, further comprising:
    receiving the pulses of EUV illumination from the plurality of illumination sources utilizing a plurality of collector mirror facets; and directing the pulses of EUV illumination from the plurality of collector mirror facets to the multiplexing mirror system.

21. The method of claim 15, further comprising:
converging portions of EUV illumination received from the plurality of pupil mirror facets utilizing a condenser disposed along the delivery path; and
illuminating the reticle with the converged portions of EUV illumination.

22. The method of claim 15, further comprising:
converging portions of EUV illumination received from the plurality of field mirror facets utilizing the pupil mirror facets; and
illuminating the reticle with the converged portions of EUV illumination.

23. A system for inspecting at least one reticle, comprising:
a stage configured to support a reticle;
a plurality of illumination sources;
a multiplexing mirror system configured to receive pulses of illumination from the plurality of illumination sources, and further configured to direct the pulses of illumination along an illumination path;
a plurality of field mirror facets, each configured to receive a portion of illumination from the illumination path;
a plurality of pupil mirror facets, each configured to receive a portion of illumination reflected from the plurality of field mirror facets, and further configured to direct the portion of illumination received from the plurality of field mirror facets along a delivery path to the reticle;
at least one detector configured to receive illumination reflected by the reticle along a collection path; and
a computing system in communication with the at least one detector, the computing system configured to locate a defect of the reticle utilizing information associated with the illumination received by the at least one detector.

24. The system of claim 23, wherein the plurality of illumination sources are configured to provide illumination at one or more wavelengths in the range of approximately 5 nm to 124 nm.

25. The system of claim 23, wherein the multiplexing mirror system includes a plurality of actuatable mirror facets, wherein the multiplexing mirror system is configured to receive each pulse of illumination utilizing a mirror facet with a selected angle of incidence.

26. The system of claim 25, wherein the plurality of actuatable mirror facets includes a rotatable polygon mirror.

27. The system of claim 23, wherein the plurality of pupil mirror facets are configured to direct overlapped portions of illumination received from the plurality of field mirror facets along the delivery path to the reticle.

28. The system of claim 23, further comprising:
an aperture disposed along the illumination path, the aperture configured to allow at least a portion of illumination from the plurality of illumination sources to flow through the aperture along the illumination path, and further configured to block particles emitted by the plurality of illumination sources from flowing along at least a portion of the illumination path.

29. The system of claim 23, further comprising:
a plurality of collector mirror facets configured to receive the pulses of illumination from the plurality of illumination sources, and further configured to direct the pulses of illumination to the multiplexing mirror system.

30. The system of claim 23, further comprising:
a condenser disposed along the delivery path, the condenser configured to converge portions of illumination received from the plurality of pupil mirror facets, and further configured to illuminate the reticle with the converged portions of illumination.

31. The system of claim 23, wherein the plurality of pupil mirror facets are configured to converge portions of illumination received from the plurality of field mirror facets, and further configured to illuminate the reticle with the converged portions of illumination.

32. The system of claim 23, wherein the at least one detector includes at least one of a time delay integration (TDI) camera and a TDI array.

\* \* \* \* \*